(12) United States Patent
Schultz et al.

(10) Patent No.: US 8,058,024 B2
(45) Date of Patent: Nov. 15, 2011

(54) DEVICES FOR THE DETECTION OF THE PRESENCE AND/OR ACTIVITY OF PROTEASES IN BIOLOGICAL SAMPLES

(75) Inventors: Gregory S. Schultz, Gainesville, FL (US); John I. Azeke, Gainesville, FL (US); Daniel J. Gibson, Gainesville, FL (US); Olajompo B. Moloye, Neshanic Station, NJ (US); Priscilla Lorraine Phillips, Gainesville, FL (US); Weihong Tan, Gainesville, FL (US); Christopher D. Batich, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 308 days.

(21) Appl. No.: 12/316,705

(22) Filed: Dec. 15, 2008

(65) Prior Publication Data

US 2009/0258382 A1 Oct. 15, 2009

Related U.S. Application Data

(60) Provisional application No. 61/137,192, filed on Jul. 28, 2008, provisional application No. 61/008,001, filed on Dec. 15, 2007.

(51) Int. Cl.
*C12Q 1/37* (2006.01)
(52) U.S. Cl. ........................................................ 435/23
(58) Field of Classification Search ................... 435/23
See application file for complete search history.

(56) References Cited

U.S. PATENT DOCUMENTS 5,000,193 A 3/1991 Heelis et al.

FOREIGN PATENT DOCUMENTS

| | | |
|---|---|---|
| EP | 0864864 | 9/1998 |
| GB | 2418145 | 3/2006 |

OTHER PUBLICATIONS

Gillard et al. "Matrix metalloproteinase activity and immunohistochemical profile of matrix metalloproteinase-2 and -9 and tissue inhibitor of metalloproteinase-1 during human dermal wound healing", Wound Rep Reg. 2004, 12:295-304.*
Tregove et al. "Analysis of the acute and chronic wound environments:the role of proteases and their inhibitors", Wound Rep Reg. 1999, 7:442-452.*
Gibson et al. "Chronic wound diagnostic for matrix metalloproteinase", Wound Healing Southern Africa, 2009, 2(2):68-70.*
Lombard et al. Assays of matrix metalloproteinases (MMPs) activities: a review. Biochimie, 2005, 87:265-272.*
Beekman et al., "Convenient fluorometric assay for matrix metalloproteinase activity and its application in biological media", *FEBS Letters*, 1996, vol. 390, pp. 221-225.
Fairclough et al., "The Use of Singlet-Singlet Energy Transfer to Study Macromolecular Assemblies", *Methods in Enzymology*, 1978, vol. 48, pp. 347-379.
Hu et al. "Inhibitors of gelatinase B/matrix metalloproteinase-9 activity comparison of a peptidomimetic and polyhistidine with single-chain derivatives of a neutralizing monoclonal antibody" *Biochemical Pharmacology*, Mar. 2004, pp. 1001-1009, vol. 67, No. 5.
Johnson et al. "A high-throughput screening approach to anthrax lethal factor inhibition" *Bioorganic Chemistry*, Aug. 2007, pp. 306-312, vol. 35, No. 4.
Knäuper et al., "Biochemical Characterization of Human Collagenase-3", *The Journal of Biological Chemistry*, 1996, vol. 271, pp. 1544-1550.
Lombard et al. "Assays of matrix metalloproteinases (MMPs) activities: a review" *Biochimie*, Mar. 2005, pp. 265-272, vol. 87, Nos. 3-4.
Matayoshi et al., "Novel Fluorogenic Substrates for Assaying Retroviral Proteases by Resonance Energy Transfer", *Science*, 1990, vol. 247, No. 4945, pp. 954-958.
Quesada et al., "Evaluation of fluorometric and zymographic methods as activity assays for stromelysins and gelatinases", *Clinical and Experimental Metastasis*, 1997, vol. 15, pp. 26-32.
Rakhmanova et al. "Assay: new substrates for FRET-based assays: use of a long-wavelength fluorophore to detect activity of MMPs" *Genetic Engineering & Biotechnology News*, Oct. 15, 2007, vol. 27, No. 18, retrieved from http://www.genengnews.com/articles/chtitem_print.aspx?tid=2243&chid=O, 3 pages total.
Rosa-Bauzá et al., "Straightforward Preparation and Assay of Aspartyl Protease Substrates with an Internal Thioester Linkage", *ChemBioChem*, 2007, vol. 8, pp. 981-984.
Stein et al., "Thioester Hydrolysis by Matrix Metalloproteinases", *Archives of Biochemistry and Biophysics*, 1994, vol. 308, No. 1, pp. 274-277.
Stryer et al., "Fluorescence Energy Transfer as a Spectroscopic Ruler", *Ann. Rev. Biochem.*, 1978, vol. 47, pp. 819-846.
Yang et al. "Detection of MMP activity in living cells by a genetically encoded surface-displayed FRET sensor" *Biochimica et Biophysica Acta*, Mar. 2007, pp. 400-407, vol. 1773, No. 3.
Yaron et al., "Intramolecularly Quenched Fluorogenic Substrates for Hydrolytic Enzymes", *Analytical Biochemistry*, 1979, vol. 95, pp. 228-235.
Baker, E. et al., "Profiles of matrix metalloproteinases and their tissue inhibitors in intraperitoneal drainage fluid: relationship to wound healing," *Wound Repair and Regeneration*, 2003, pp. 268-274, vol. 11, No. 4.
Gibson, D. et al., "Adaptation of a bench-top protease assay for use as a rapid and non-instrumented bedside test of wound fluid protease activity," *Wound Repair and Regeneration*, 2008, pp. A18, vol. 16, No. 2.
Mittoo, S. et al., "Synthesis and evaluation of fluorescent probes for the detection of calpain activity," *Analytical Biochemistry*, 2003, pp. 234-238, vol. 319, No. 2.
Moloye, O. et al., "Development of thin films for rapid detection of matrix metalloproteinases in wound fluids," *Wound Repair and Regeneration*, 2008, pp. A39, vol. 16, No. 2.

\* cited by examiner

*Primary Examiner* — Amber D. Steele
*Assistant Examiner* — Bin Shen
(74) *Attorney, Agent, or Firm* — Saliwanchik, Lloyd & Eisenchenk (57) ABSTRACT

The subject invention provides novel devices and methods for the detection of the presence and/or activity of proteases in biological samples.

18 Claims, 7 Drawing Sheets
(7 of 7 Drawing Sheet(s) Filed in Color)

DEVICES FOR THE DETECTION OF THE PRESENCE AND/OR ACTIVITY OF PROTEASES IN BIOLOGICAL SAMPLES

CROSS-REFERENCE TO A RELATED APPLICATION

The subject application claims the benefit of U.S. Provisional Application 61/008,001, filed Dec. 15, 2007 and U.S. Provisional Application 61/137,192, filed Jul. 28, 2008, in their entirety.

BACKGROUND OF THE INVENTION

The rapid and accurate detection of target molecules is critical for many areas of research and medical diagnosis. Important features for a diagnostic technique to be used for the detection of analytes are specificity, speed, and sensitivity. Time constraints and ease of on-site analysis can be major limitations.

Most assay systems can be characterized as having three key components: a probe that recognizes the target analyte(s) with a high degree of specificity; a reporter that provides a signal that is qualitatively or quantitatively related to the presence of the target analyte; and a detection system capable of relaying information from the reporter to a mode of interpretation. The probe (e.g., antibody, nucleic acid sequence, or enzyme product/activity) should interact uniquely and with high affinity to the target analyte(s), but not with non-targets. In order to minimize false positive responses, it should not react with non-targets.

The label is often directly or indirectly coupled (conjugated) to the probe, providing a signal that is related to the concentration of analyte upon completion of the assay. The label should not be subject to signal interference from the surrounding matrix, either in the form of signal loss from extinction or by competition from non-specific signal (noise) from other materials in the system.

The detector is usually a device or instrument used to determine the presence of the reporter (and therefore analyte) in the sample. Ideally, the detector should provide an accurate and precise quantitative scale for the measurement of the analyte. In rapid on-site tests, such as pregnancy tests, the detection instrument is the human eye and the test results are qualitative (positive or negative).

Proteases are implicated in disparate pathologies including: virulence factors that facilitate infectious diseases (Matayoshi, E. D. et al. *Science*, 247 (February 1990): 954-958; Sham, H. L. et al. *Journal of Medicinal Chemistry*, 39, no. 2 (1996): 392-397; Sham, H. L. et al. *Antimicrobial Agents and Chemotherapy*, 42, no. 12 (1998): 3218-3224), metastasis of cancerous cells (McCawley, L. J. and L. M. Matrisian *Current Opinion in Cell Biology*, 13 (2001): 534-540), tissue damage in periodontal disease (Sandholm, L. *Journal of Clinical Periodontology*, 13, no. 1 (1986): 19-26), complications in pregnancy (Locksmith, G. J. et al. *Am J Obstet Gynecol*, 184, no. 2 (January 2001): 159-164), tissue destruction in inflamed joints (Cunnane, G. et al. *Arthritis & Rheumatism*, 44, no. 8 (2001): 1744-1753), and destruction of pro-healing factors and nascent tissue in chronic, non-healing, wounds (Ladwig, G. P. et al. *Wound Repair and Regeneration*, 10 (2002): 26-37; Trengove, N. J. et al. *Wound Repair and Regeneration*, 7 (1999): 442-452; Yager, D. R. et al. *Wound Repair and Regeneration*, 5 (1997): 23-32).

Studies of proteases in diseases have employed tests from one of two (or a combination of the two) classes: molecular presence-based tests, or catalytic activity-based tests. A common molecular presence-based test would be an immunodetection assay where the protease of interest is isolated from the rest of the sample and antibodies that specifically recognize that protease are labeled with a detectable agent. The other class, catalytic activity-based, does not just measure whether the molecule (or the portion of the molecule that an antibody recognizes) is present, it measures how active the molecule is in the given conditions.

Currently, three protease activity based assays are in common laboratory use: the zymogram (Quesada, A. R. et al. *Clin. Exp. Metastasis*, 15 (1997): 26-32), the thiopeptolide continuous colorimetric assay (Stein, R. L. and M. Izquierdo-Martin *Archives of Biochemistry and Biophysics*, 308, no. 1 (January 1994): 274-277; Oxford Biomedical Research. *Colorimetric Drug Discovery Assay for Matrix Metalloproteinase-7*, Product Brochure, Oxford, Mich.: Oxford Biomedical Research, 2005 Oxford Biomedical Research. *Colorimetric Drug Discovery Assay for Matrix Metalloproteinase-7*, Product Brochure, Oxford, Mich.: Oxford Biomedical Research, 2005; Rosa-Bauza, Y. T. et al. *ChemBioChem*, 8 (2007): 981-984), and the fluorescence resonance energy transfer (FRET) continuous fluorometric assay (Fairclough, R. H. and C. R. Cantor *Methods in Enzymology*, 48 (1978): 347-379; Stryer, L. *Annu Rev Biochem*, 47 (1978): 819-846; Yaron, A. et al. *Analytical Biochemistry*, 95, no. 1 (May 1979): 228-235; Matayoshi, E. D. et al. *Science*, 247 (February 1990): 954-958; Beekman, B. et al. *FEBS Letters*, 390, no. 2 (1996): 221-225; Knäuper, V. et al. *The Journal of Biological Chemistry*, 271, no. 3 (January 1996): 1544-1550).

The zymogram is usually used when analyzing mixtures of proteases since it first resolves the different proteases by mass and then measures their activity. The thiopeptolide assay is used by suppliers of proteases to verify/guarantee a basic level of protease activity in the supplied sample (Calbiochem Data Sheet PF024 Rev. 25-September-06 RFH) (Biomol Product Data Catalog No.: SE-244).

Many currently marketed rapid, point-of-care diagnostic technologies are limited by their analytical sensitivity or by the number of analytes detected in a single assay.

BRIEF SUMMARY OF THE INVENTION

The present invention provides diagnostic methods and devices that can be used to assay a medium, such as tissue in vivo or a sample in vitro (e.g., biological sample or environmental sample), in order to determine the presence, quantity, and/or concentration ratio of one or more proteases.

The proteases detected according to the subject invention can be biochemical markers of health that can be used to direct therapy or prophylaxis. Thus, the devices and methods of the invention can be of great benefit when diagnosing (and implementing a treatment for) a pathological condition that has one or more biochemical markers.

For example, a non-healing (chronic) wound is marked by the imbalance of several biological regulators, such as proteases, and protease inhibitors, representing target analytes for the assays of the present invention. In preferred embodiments exemplified herein, the subject invention provides assays for the detection and/or quantification of matrix metalloproteinase (MMP) activity at the site of a wound.

In a specific embodiment exemplified herein, the subject invention provides a rapid and accurate assay for qualitatively and/or quantitatively assessing the presence of one or more MMPs in a sample taken from a wound. Specifically exemplified herein is a FRET assay that, through a unique and advantageous combination of substrate, fluorophore, and quencher is able to quickly and accurately assess the presence and, optionally, the quantity, of MMP in a sample taken from a wound.

Advantageously, in certain embodiments, the subject invention provides assays that can be self-contained in a single unit. This facilitates conducting assays in the field and, in the case of healthcare, at the point of care.

In an embodiment that is specifically exemplified herein, the subject invention provides assays that can be used to determine and/or monitor the status of a wound, thereby facilitating the administration of appropriate care and treatment. The assays are quick and easy-to-use. In specific embodiments the assay can be carried out by, for example, a nurse utilizing either no instrumentation or only minimal instrumentation. In one embodiment, information about the status of a wound can be readily, easily and reliably generated in 10 minutes or less. Information about the wound can include, but is not limited to, protease presence and/or activity. Particularly preferred assays as described herein include, substrate cleavage assays.

Assay formats that can be used in accordance with the subject invention include, but are not limited to, FRET and colorimetric assays.

Target analytes can be endogenous or exogenous to the medium to be assayed. For example, a target molecule can be a protease inhibitor that is normally found in the tissue or at an anatomical sample site. In another embodiment, a target molecule is exogenous to the tissue or sample site, e.g., having been administered to the subject for the purpose of treatment or prophylaxis. For example, proteases regulate many physiological processes by controlling the activation, synthesis and turnover of proteins. Many small molecules have been shown to effectively inhibit these enzymes and exert pharmacological properties (Abbenante and Fairlie, *Medicinal Chemistry*, 2005, 1:71-104). Thus, the target molecule can be a protease inhibitor, such as the broad spectrum metalloproteinase inhibitor GM6001 (also known as Ilomastat or Galardin), which is not normally found in the body.

In one embodiment, the subject invention provides methods and devices for assessing the topographical distribution of proteases in wounds using a thin film diagnostic device. This diagnostic technology provides a point-of-care wound diagnostic tool that aids physicians in assessing the presence of proteases that may be contributing to a patient's poor healing condition. Thus the use of this device can aid in, for example, chronic wound treatment.

In one embodiment, the present invention is useful for differential assays, in which a comparison between the amounts of multiple target molecules in the same sample or site is of interest.

Upon conducting the simple procedures of the subject invention, the physician has very important information to not only treat the condition in an as-needed manner, but can also be used to design and justify subsequent and related treatments as required by the majority of insurance corporations today. The assays of the subject invention can also be used prior to the application of exogenous proteins and/or grafts to ensure that the recipient site is conducive to the therapy (e.g. any tissue or protein applied to the site will not be adversely affected by the presence of proteases).

BRIEF DESCRIPTION OF THE SEQUENCES

SEQ ID NO:1 is a peptide substrate useful according to the subject invention.

BRIEF DESCRIPTION OF THE DRAWINGS

The file of this patent contains at least one drawing executed in color. Copies of this patent with color drawings(s) will be provided by the Patent and Trademark Office upon request and payment of the necessary fee.

DETAILED DESCRIPTION OF THE INVENTION

The present invention provides diagnostic methods and devices for detecting at least one protease in a sample. The sample may be, for example, an in vivo tissue sample or an in vitro sample (e.g., biological sample or environmental sample). The method and devices disclosed herein can be used to determine the presence, quantity, and/or concentration ratio of one or more target proteases.

Advantageously, in certain embodiments, the subject invention provides assays that can be self-contained in a single unit. This facilitates conducting assays in the field and, in the case of healthcare, at the point of care.

The analytes detected according to the subject invention can be biochemical markers of health that can be used to direct therapy or prophylaxis. Thus, the assays of the subject invention can be used as part of a program to optimize (or at least improve) treating and/or routing in a hospital. In a preferred embodiment the assays of the subject invention are used to detect and/or quantify proteases present in a wound. Specifically exemplified herein are assays for MMP-9.

The MMP-assay of the subject invention is particularly advantageous because, through the careful selection of various parameters, including the substrates, fluorophore and quenchers the assay exhibits rapid kinetics with excellent accuracy and minimal background interference.

The devices and methods of the invention can be of great benefit when diagnosing a pathological condition that has one or more biochemical markers. For example, a non-healing (chronic) wound is marked by the imbalance of several biological regulators, such as cytokines, proteases, and protease inhibitors, representing potential target analytes for the assays of the present invention. In one embodiment, the present invention is particularly useful for differential assays, in which a comparison between the amounts of multiple target molecules in the same sample or site is of interest.

In an embodiment that is specifically exemplified herein, the subject invention provides assays that can be used to determine and/or monitor the status of a wound. The assays are quick and easy-to-use. In specific embodiments, the assay can be carried out by, for example, a nurse utilizing either no instrumentation or only minimal instrumentation. In one embodiment, information about the status of a wound can be readily, easily and reliably generated in 30 minutes or less. In a preferred embodiment, the results are obtained in 15 minutes or less. Most preferably, the results are generated in 10 minutes or less. Information about the wound can include, but is not limited to, protease activity and/or presence.

With regard to protease activity, the activity of MMP-2, MMP-8, MMP-9 and elastase are of particular interest in wound care. In a specific embodiment, the assays of the subject invention are utilized to assess the status of chronic wounds by determining the presence, activity and/or quantity of one or more of those proteases. As used herein, reference to "chronic wounds" refers to wounds that after 2 weeks are not healing properly.

In a preferred embodiment, the subject invention utilizes a catalytic activity-based protease assay. This assay is advantageous because the pathogenic consequences of proteases are based on the activity of the proteases. This activity is difficult, if not impossible, to discern with molecular presence based assays.

A variety of assay formats can be used according to the subject invention. Particularly preferred assays as described herein include FRET and calorimetric assays. Preferably, the assays are substrate cleavage assays.

A further assay format utilizes a thin film (similar to x-ray films) for the detection of proteases. In this context, the thin film can be, or can comprise, a hydrolyzable substrate for the purpose of detecting a protease.

The subject invention also provides sample collection methodologies which, when combined with the assays of the subject invention, provide a highly advantageous system for analyte evaluation in a wide variety of settings. In one embodiment, a "swab-in-a-straw" collection and assay system can be utilized as described herein.

Due to their ability to easily, quickly and accurately determine the presence, quantity, and/or concentration ratio of single or multiple target analytes, the devices and methods of the invention facilitate medical diagnoses at a physician's office and/or at the bedside of the patient. Ex vivo analysis of bodily fluids utilizing a device and method of the invention can be applied to a wide range of diagnostic tests. Analysis of bodily fluid samples using a device or method of the present invention can enable timely interventions for time-sensitive conditions or diseases.

The devices and methods of the invention can also be used for ocular applications, e.g., to assess the presence of ocular infection or molecules that are of diagnostic value in assessing infected and/or inflamed eyes. The molecule(s) targeted for detection and/or measurement can be for example, proteases and/or protease inhibitors.

The devices and methods of the subject invention can also be used for urological and/or gynecological applications, e.g., to assess the presence of urological and/or genital biomarkers.

The devices and methods of the invention can be used for obstetrical applications, e.g., to assess molecular risk factors for miscarriage or premature birth. The molecule(s) targeted for detection and/or measurement can be molecules known to be associated with premature rupture of membranes (PROM), such as matrix metalloproteinases (MMPs) and MMP inhibitors.

Another aspect of the invention concerns methods and devices for simultaneously detecting and measuring the relative amounts of multiple target molecules in a medium, or sample thereof, comprising contacting a device of the invention with the medium under conditions sufficient for the target molecules to be detected, if present. Preferably, the concentration of each target molecule is determined, relative to each other target molecule, and provided by a quantitative or semi-quantitative signal that is readily observable.

The devices and methods of the invention can be used for dermal applications, e.g., to assess the presence of analytes in tissue or wound fluids that are of diagnostic value in assessing wound healing. The molecule(s) targeted for detection and/or measurement can be, for example, proteases or protease inhibitors.

If it is sufficient to detect the presence of a protease, one embodiment of the subject invention can utilize a device that functions based on lateral flow strip technology. This technology can be used to, for example, indirectly measure MMP activity by quantifying it with respect to its natural inhibitor. In a specific example, the ratio of MMP-9/TIMP-1 can be evaluated.

Optionally, in the various embodiments of the invention, the diagnostic method further comprises comparing the concentration of the target molecule in the medium (e.g., a bodily fluid), as determined above, to pre-existing data characterizing the medium (e.g., concentration of the same target molecule in the same patient or a different patient). The target molecule concentration may be that specific target molecule concentration observed under particular conditions.

Optionally, the method of the invention further comprises monitoring the presence and/or concentration of one or more target molecules in a medium over a period of time.

Simple "mix-and-read" assays minimize time and increase productivity; assays can be for naked eye or quantitative assessment using well established, relatively inexpensive detection technologies; easy-to-interpret detection system when used by non-technical personnel. Advantageously, less equipment and fewer lab skills are necessary to conduct the assays.

Assays that can be used according to the subject invention to assay for protease activity include assays based on specific cleavage of a substrate and, optionally, separation of a product. These assays may be, for example, FRET assays, colorimetric assays or assays based on digestion of thin films.

Each of these assay formats are discussed in more detail below.

Substrate Cleavage Assays

The enzymatic activity of proteases can be determined using substrate cleavage assays wherein a proteolytic activity of the sample is determined by monitoring the cleavage of a model peptide introduced into the sample.

The system can, for example, comprise a microparticle having bound to its surface a large number of a dye-conjugated substrates. The microparticles are of sufficient density that, when dispersed in the assay solution, their settling rate is of the order of 5-10 minutes.

The substrate is a natural or synthetic peptide sequence having a generic or highly enzyme-specific sequence. As such, the degree of enzyme specificity can be tuned to monitor the activity of a group of proteases or that of a single protease of interest. Finally, tethered to the substrate sequences are dye subunits which may be composed of single or multiple (e.g. dendritic, oligomeric, etc.) dye molecules conjugated to the free end of the substrate.

At t=0, the microparticles are exposed to the sample in a suitable assay buffer solution that is then mixed thoroughly to bring the particles into suspension. As the dense particles settle over the next 5-10 minutes, the proteases present in the sample cleave their substrate targets, thus allowing the dye molecules to enter solution and produce a detectable optical change of the assay solution.

If insufficient enzyme activity is present in the sample, the microparticles settle out of solution with their attached substrate-dye appendages and the assay buffer remains clear. The critical dye concentration required for the detection of sufficient enzymatic activity can be determined for a number of systems (i.e. naked eye or automated detection systems). Thus, the system is highly tunable for a number of single or multiplexed assays involving various critical enzyme concentrations of one or several proteases.

The proteolytic detection assays of the subject invention can be used to measure the protease levels in wound fluids, which is an indicator of anticipated healing or chronicity. Additionally, prior to attaching a graft or treating with a growth factor the nurse/doctor can ensure that the host environment is amenable to the graft/growth factor (i.e. that the graft/growth factor will not be destroyed).

In this embodiment a peptide can be used that is similar to the FRET peptide with the quencher replaced with a dye/signal generator and the opposing terminus (other side of scissile bond) containing an affinity tag.
 a. Biotin
 b. Peptide sequence for which an antibody has been generated
  i. FLAG
  ii. HA
 c. polyHis tag In one embodiment, the assay of the subject invention involves measurement of proteases, such as MMPs, using a synthetic substrate that is coupled to a reporter enzyme, which can then be measured spectrophotometrically. In one embodiment the reporter enzyme can be glucose oxidase. This provides another method for generating a product that is released from the synthetic peptide after cleavage by an MMP, or other protease.

The structure of the substrate can be similar to the dye-coupled peptide substrate except the dye is replaced by the enzyme (i.e., glucose oxidase).

A. FRET

The basis of the FRET assay is to bring a fluorescing dye close enough to a dye that prevents fluorescence (quencher) by coupling the dyes to a peptide that is a substrate for the protease being tested. Once the protease has severed the peptide the fluorescing dye can now separate far enough away from the quencher to produce a detectable signal.

The peptide joining the dye and quencher can be modified to produce specificity for the protease being measured. In a specific example, the DABCYL absorbs the color that EDANS fluoresces thereby preventing its detection.

In addition to quenching, FRET can be used to cause a change in fluorescing color. An example is when a green fluorescing molecule is close to a red fluorescing molecule. If a green-exciting light (i.e. blue) is introduced, the green fluorescence is the source of green light to excite the red fluorophore. When they drift, the green light can escape and not be a source of excitation for the red fluorophore. This is an example of a visually interpretable assay (i.e. red to green shift).

In general, the mechanics for the quenching can vary depending on the dye and quencher combination, but the concept at the technological level remains the same. Once the peptide is cleaved the EDANS can separate far enough away from the DABCYL for the fluorescent color to escape and be detected.

Typically, a reaction between samples containing the protease of interest are mixed with these peptides. The sample can then be irradiated, preferably with non-ionizing electromagnetic radiation. The reactions are continuously monitored by a fluorimeter for a change in fluorescent intensity. The products were quantified by measuring the fluorescence of a known quantity of the dye, and then scaled by the difference in fluorescence between free dye and the peptide fragment bound dye.

Advantageously, the specificity for these assays is provided by the choice of a soluble peptide substrate that is specifically cleaved by the target protease. The output from this assay can be one or more of the following:

a. LED or filtered white light excitation
  i. UV LED (<380 nm) for blue-fluorescing fluorophores, and for most fluorophores in general (Blue, most others)
  ii. Blue/Cyan LED (450-495 nm) for green-fluorescing based fluorophores
   (Green/yellow)
  iii. Green LED (540-560 nm) for red-fluorescing fluorophores (Red)
  iv. Red LED (582 nm) for infrared read out
 b. Read either by eye or with fluorimeter
  i. Eye
   1. Yes/No
   2. Semiquantitative scale
    a. Similar to pool chemistry where color/opacity scale is provided for comparison
  ii. Fluorimeter
   1. Quantitative via any available photon counting elements
    a. CMOS-based
    b. CCD-based
    c. Photodiode-based
    d. Photoresistor-based Advantageously, due to the narrow spectrum used to excite the dyes, interference due to visibly colored agents (such as hemoglobin) is effectively circumvented. For instance, with fluorescein excitation via blue light, the hemoglobin cannot be seen because it does not scatter/reflect blue light.

Another embodiment of the invention is a device for use in a FRET assay that utilizes chemilumenescent excitation (2,4-Dinitrophenyl oxalate via $H_2O_2$, for example) of the fluorophore upon cleavage. Advantageously, this makes the FRET assay an instrument free assay.

B. Thin Film Assays

In one embodiment, the subject invention provides a rapid and simple method of assessing the protease activities in biological samples using a pigmented substrate thin film.

Various dyes, including Coommassie, readily bind to undigested proteins in solution. This phenomenon has been employed in routine laboratory techniques including sodium dodecyl sulfate polyacrylamide gel electrophoresis (SDS-PAGE) and zymography. In these laboratory methods, gels are stained to visualize electrophoretically separated proteins or regions of protein digestion by enzyme activity, respectively.

In accordance with the subject invention, chromo/fluorometrically labeled thin films of target substrates can be cast by a number of methods, including spin-coating, dip-coating, and tape-casting. Digestion of the target substrate can be visualized in minutes by simply reacting a volume of the biological sample onto the surface of the film and rinsing in water to remove the liberated dye and protease. The film may be, for example, gelatin, albumin, casein, fibrin, a synthetic peptide, or other substrate cleaved by the protease of interest.

The protease activity in the assay degrades a thin film of opaque/tinted/dyed substrate increasing the contrast between protease exposed area and the unexposed/degraded region surrounding it. In one embodiment, the area of exposure can have a non-cleavable message/text that can be revealed as the area around it loses opacity due to protease activity. The gain in contrast makes the message readable and can include numbers for quantification, control status, and/or diagnosis/clinical suggestion.

Biological Samples

The devices and methods of the subject invention can be used to detect and/or quantify the presence and/or activity of proteases in a variety of biological samples. The devices according to the subject can be used to assay various samples as follows:

A. Wound Fluids (Chronic Wounds)
   Obtained by:
    1. Swab
    2 Vac
    3. Bandage/dressing
    4. Capillary/pipette
    5. Syringe
    6. Test run in-vivo in the wound
    7. Tissue biopsy B. Tear Fluid
   Obtained by:
    1. Wicking paper/material
    2. Capillary/pipette
    3. Syringe C. Vaginal Fluid
   Obtained by:
    1. Swab
    2. Capillary/pipette
    3. Panty liner
    4. Tampon
    5. Wicking paper/material
    6. Syringe
    7. Tissue biopsy D. Oral Fluids
   1. Saliva
    Obtained by:
     a. Patient spitting into adequate receptacle
     b. Cheek swab
     c. Capillary/pipette
     d. Wicking paper/material
     e. Syringe
     f. Tissue biopsy
   2. Crevicular Fluid (periodontal Space)
    Obtained by:
     a. Syringe
     b. Capillary/pipette
     c. Collected scrapings
     d. Wicking paper/material
     e. Swab
     f. Tissue biopsy E. Nasal
   Obtained by:
    1. Collection of naturally evacuated fluids (runny nose)
    2. Forced evacuation (blowing one's nose) into adequate receptacle
    3. Swab
    4. Flushing
    5. Capillary/pipette
    6. Wicking paper/material
    7. Syringe
    8. Collection of naturally evacuated fluids (runny nose)
    9. Tissue biopsy F. Throat
   Obtained by:
    1. Forced evacuation (coughing) into/onto adequate receptacle
    2. Swab
    3. Flushing-gargling-spitting
    4. Capillary/pipette
    5. Wicking paper/material
    6. Syringe
    7. Tissue biopsy G. Otological (Ear)
   Obtained by:
    1. Swab
    2. Flushing
    3. Capillary/pipette
    4. Wicking paper/material
    5. Syringe
    6. Tissue biopsy H. Axilla
   Obtained by:
    1. Swab
    2. Flushing
    3. Capillary/pipette
    4. Wicking paper/material
    5. Syringe
    6. Clothing (sweat)
    7. Tissue biopsy I. Pulmonary (Lung)
   Obtained by:
    1. Forced evacuation (coughing) into/onto adequate receptacle
    2. Swab
    3. Capillary/pipette
    4. Wicking paper/material
    5. Syringe
    6. Vac
    7. Tissue biopsy J. Cyst
   Obtained by:
    1. Swab
    2. Capillary/pipette
    3. Wicking paper/material
    4. Syringe
    5. Vac
    6. Tissue biopsy K. Synovial Fluid/Connective Tissue
   Obtained by:
    1. Swab
    2. Capillary/pipette
    3. Wicking paper/material
    4. Syringe
    5. Vac
    6. Tissue biopsy L. Urological
   Urethra M. Feces N. Urine O. Blood P. Semen Q. Vomit

EXAMPLE 1

FRET Assay Device

Figure 1:
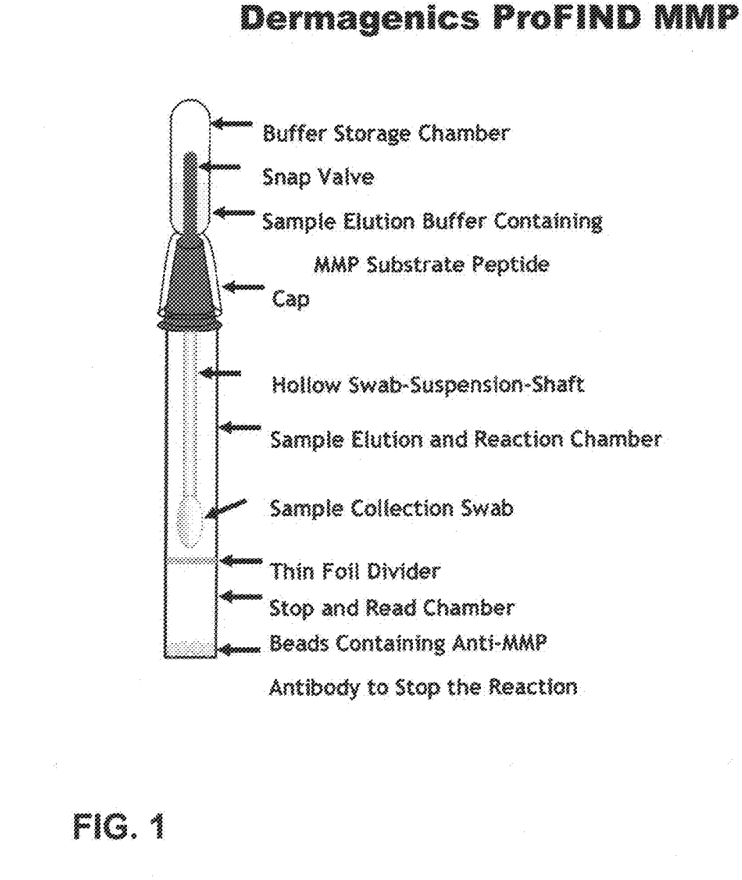
FIG. 1 shows a FRET assay device of the subject invention.

FIG. 1 shows an embodiment of a device of the subject invention based on a FRET assay format.

EXAMPLE 2

Assay Device

Figure 2:
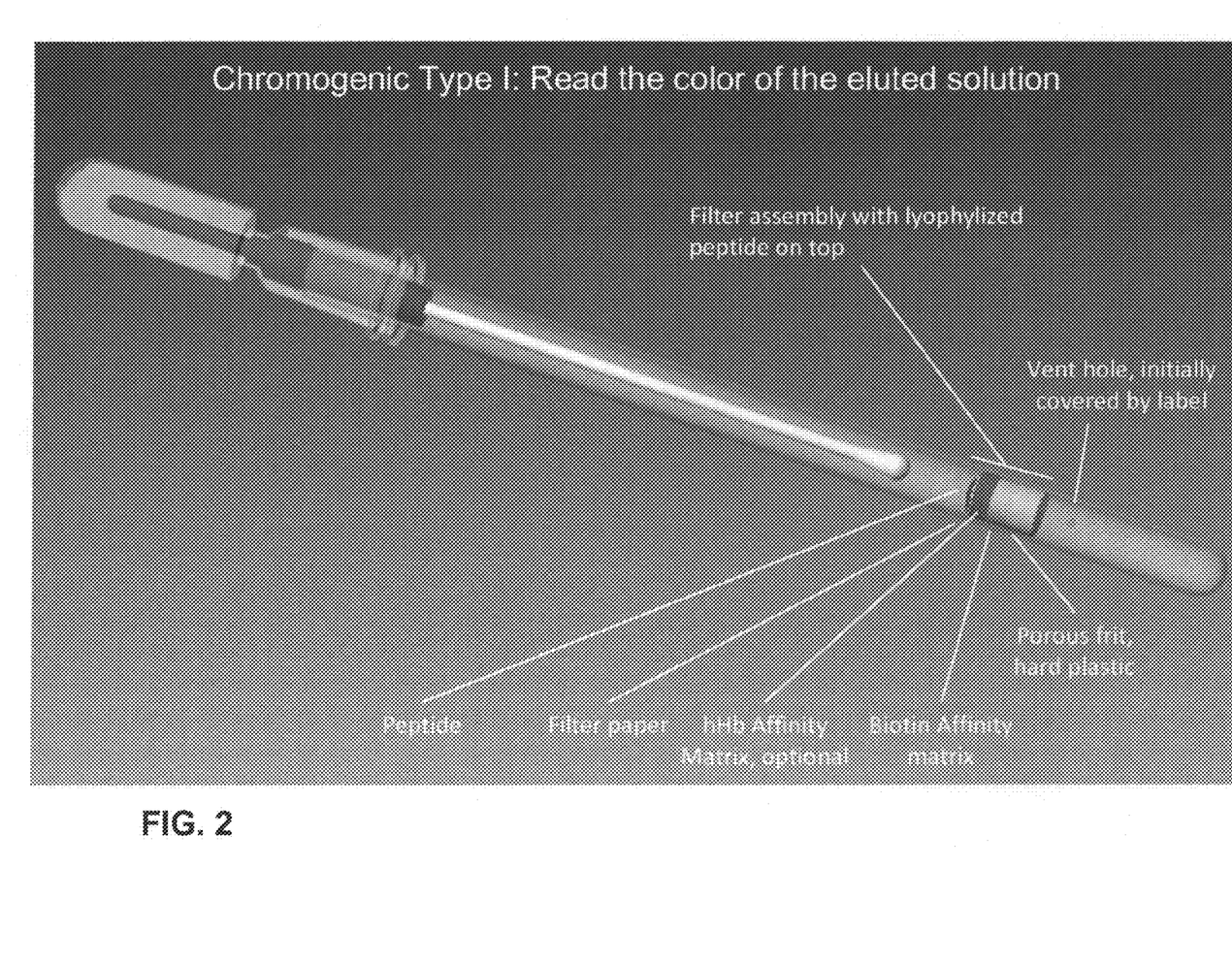
FIG. 2 shows a chromogenic type assay device of the subject invention.

FIG. 2 shows another embodiment of the device of the subject invention wherein the assay is a chromogenic type.

EXAMPLE 3

Assay Devices with Later Flow Strip-Like Format

Figure 3:
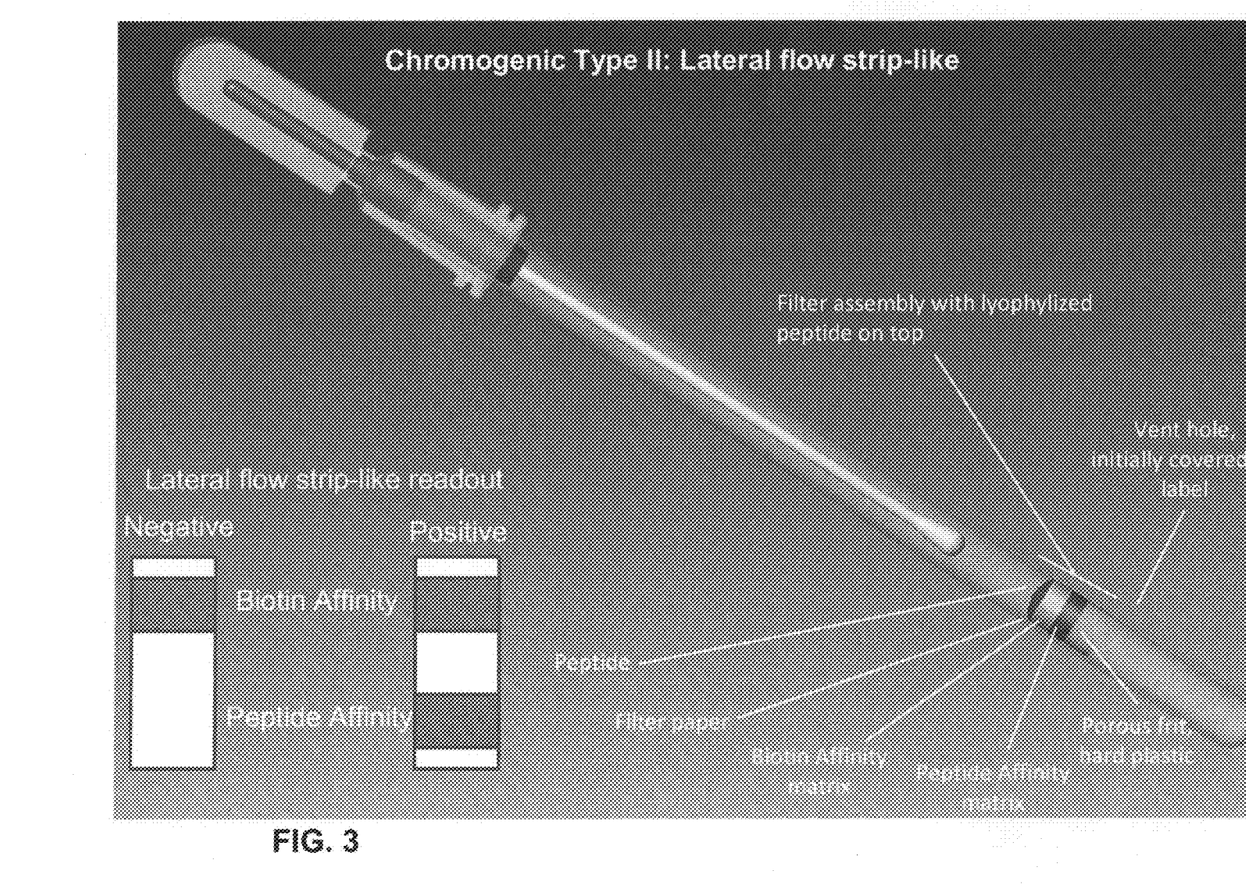
FIG. 3 shows a lateral flow strip-like assay device of the subject invention.

FIG. 3 shows an embodiment of the subject invention wherein the assay device utilizes a lateral flow strip-like format.

EXAMPLE 4

Topographical Diagnostic Device for Wound Care

In one embodiment, the subject invention provides methods and devices for assessing the topographical distribution of proteases in wounds using a thin film diagnostic device. One example of such a device is shown in FIG. 4.

Figure 4:
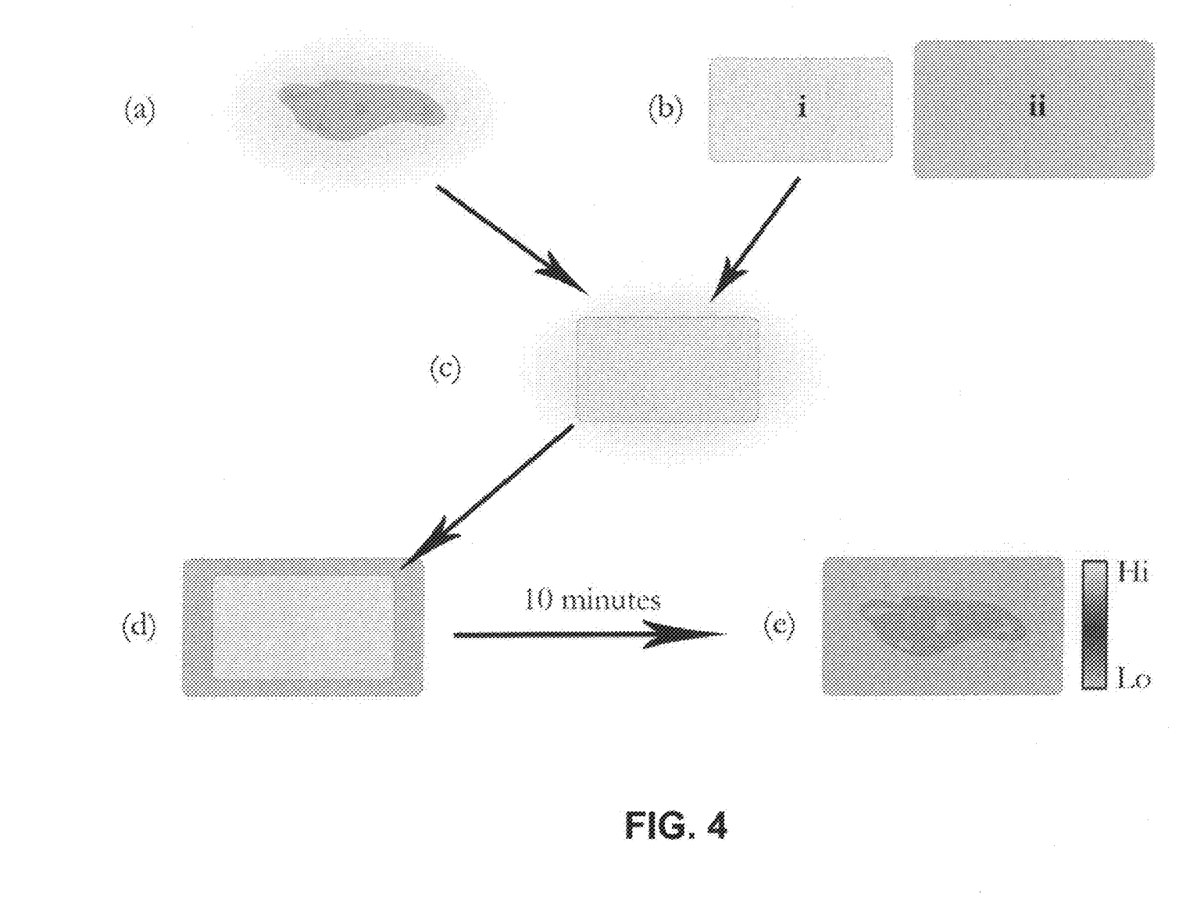
FIG. 4 shows a method of using a topographical diagnostic device for wound care.
Figure 5A:
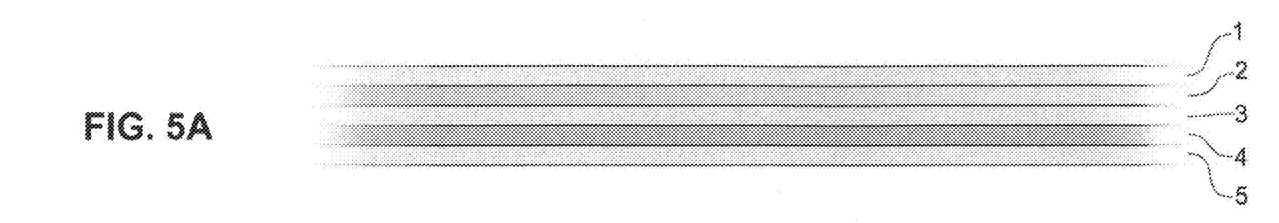
FIG. 5 shows a multilayered thin film point-of-care diagnostic for protease detection.
Figure 5B:
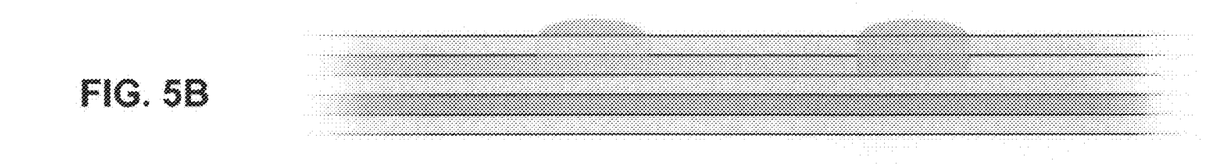
Figure 5C:
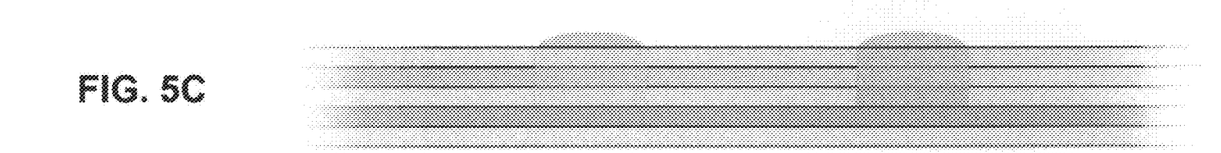
Figure 5D:
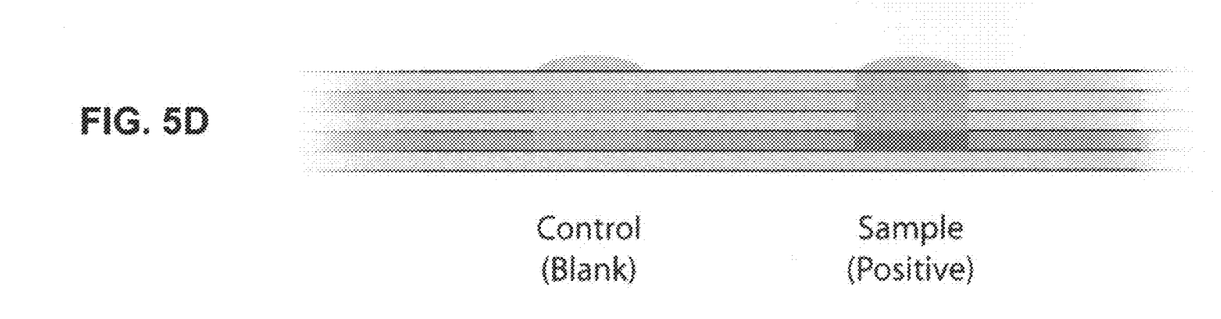

With reference to FIG. 4, upon presentation of a chronic wound (a) the caregiver applies the absorbent pad (b-i.) of the diagnostic to the wound for a specified sampling time (c). Following this, the absorbent pad is placed onto the diagnostic sheet (b-ii.).

As the sample is allowed to incubate (d), the entrapped proteases in the absorbent pad diffuse into the diagnostic sheet and react with the chemistry of the diagnostic sheet. After the designated period, which can be, for example, approximately 10 minutes, the absorbent pad is removed and the diagnostic sheet is examined for signs of protease activity (e).

Depending on the desired diagnostic properties, visualization of protease activity may be achieved by any of a number of means including, but not limited to, the naked eye, photography, fluorescence, electrochemical, electronic, or other means.

Whereas quantification of protease activities is quite possible in a topographical diagnostic, a primary purpose of this device is to determine the spatial distribution of protease activity in the wound bed.

This assay is amenable to a number of readily available technologies for assessment and archival of the topographical data. For example, chromogenic-, luminescence-, or fluorescence-based detection methods may be used in conjunction with digital photography for sensitive, intuitive observation and storage of patient care records. Finally, in addition to describing the topographical activity of a single protease, the system can be adapted to assess multiple analytes (i.e. protease, biofilm, etc.), thus providing a more complete assessment of the wound bed.

By using this device, the caregiver is able to see the biological activity present in the actual wound bed. Further, the caregiver is more readily able to see the direct impact of various treatments on the protease expression in the wound.

Advantageously, a picture of the protease imbalance in the wound serves as sufficient justification for applying more advanced wound management technologies on a case-by-case basis (i.e. advance personalized medicine).

Assays can be developed for naked eye or quantitative assessment using well-established, relatively inexpensive technical and non-technical personnel.

In addition to describing the topographical activity of a single protease, the system can be adapted to multiple analytes (i.e. proteases, biofilm, etc.), thus providing a more complete assessment of the wound bed.

EXAMPLE 5

Multilayered Thin Film Diagnostic Device

In one embodiment the subject invention provides methods of detecting proteases using a multilayered thin film diagnostic device. One embodiment of this device is shown in FIG. 5.

As shown in FIG. 5, this device can comprise various thin film layers including, for example, (1) a cover layer, (2) an enzyme layer, (3) a separation layer, and (4) a substrate layer fabricated by various thin film fabrication methods onto a suitable backing material. The cover and separation layers are optional, depending upon the application and material properties for a given system. In addition, the enzyme and substrate layers may be reversed. In a preferred embodiment, the thin film layer superior to the backing material differs from the more superficial layers such that it is less sensitive to the proteases in the sample and will not degrade significantly during the duration of the test.

Each layer superficial to Layer 4 is digestible by the proteases in the sample within the time allotted for the assay (e.g. 10 minutes) such that a critical concentration (i.e. activity) of protease breaches a threshold required for detection.

A chromogenic/luminescent/fluorescent enzyme-substrate pair is impregnated in Layers 2 and 4. These layers may be separated by a separation layer (Layer 3) and the entire device may additionally be covered by an additional layer (Layer 1). While these two layers may prove unnecessary in certain systems, they may be included in the device to improve shelf life and reduce non-specificity.

Upon application of the sample, the thin films are hydrated and the proteases proceed to digest the films, which are manufactured from various materials and chemicals that serve as a suitable substrate for the sample proteases and allow for adequately rapid digestion of each layer (seconds-to-minutes). Upon digestion of Layer 2, the entrapped enzyme (or substrate) paired with the entrapped substrate (or enzyme) impregnated in Layer 4 is liberated and continues to migrate with the fluid front as the remaining layers are hydrated and digested by the protease present in the sample. Upon reaching Layer 4, the liberated enzyme (or substrate) reacts with the entrapped substrate (or enzyme), causing a development of color/luminescence/fluorescence characteristic to the chosen enzyme-substrate system.

Because the system is engineered such that neither enzyme nor substrate is free to migrate with the fluid front in the absence of sufficient protease activity color generation is a positive indication of protease activity.

The thin film systems may be designed to allow the detection of a broad spectrum of protease activities and is capable of being sensitive to select protease classes of interest. Demonstrations of such systems are presented in FIG. 6, which shows various possible configurations of the assay.

Figure 6A:
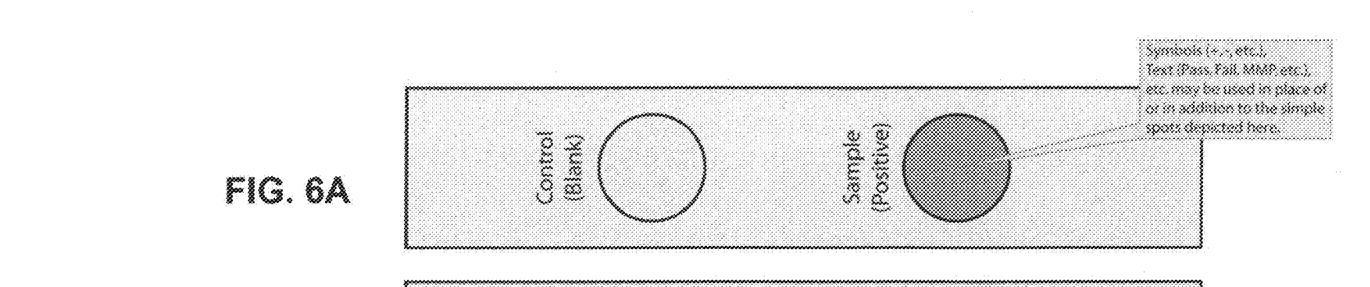
FIG. 6 shows various configurations of an assay of the subject invention.
Figures 6B, 6C:
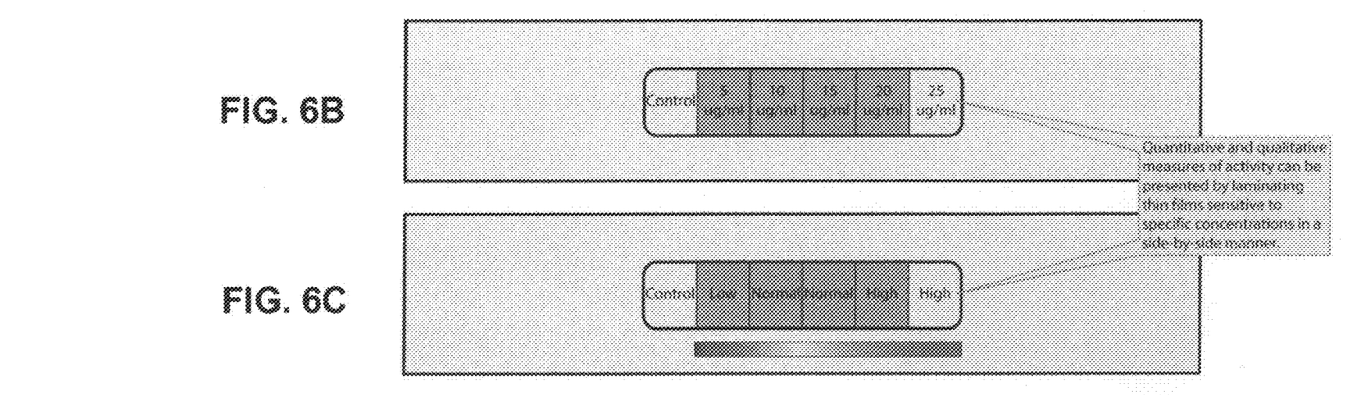
Figure 6D:
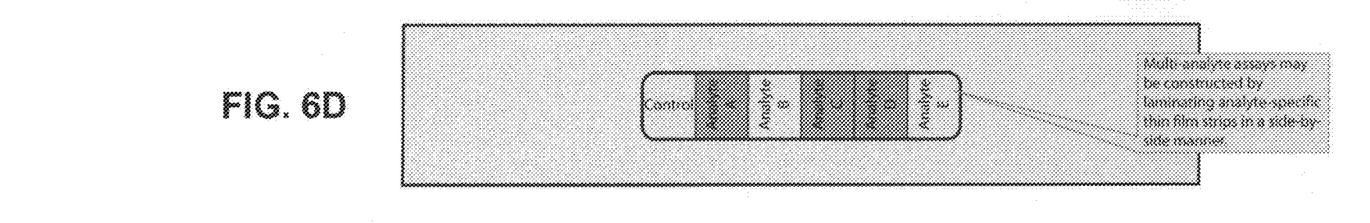

The assay may be constructed to allow for (A) Pass/Fail, (B) Quantitative, (C) Semiquantitative/Qualitative assessment. In addition, (D) multiple proteases may be assessed on a single test.

It should be noted that, although the diagnostic strips depicted in FIG. 6 are generally monolithic in nature, a large number of thin film deposition methods may be employed to produce monolithic strips in addition to multi-colored detection outputs. Furthermore, printing methods may be employed to deposit symbols, script, etc. to facilitate interpreting the assay results.

Figure 7A:
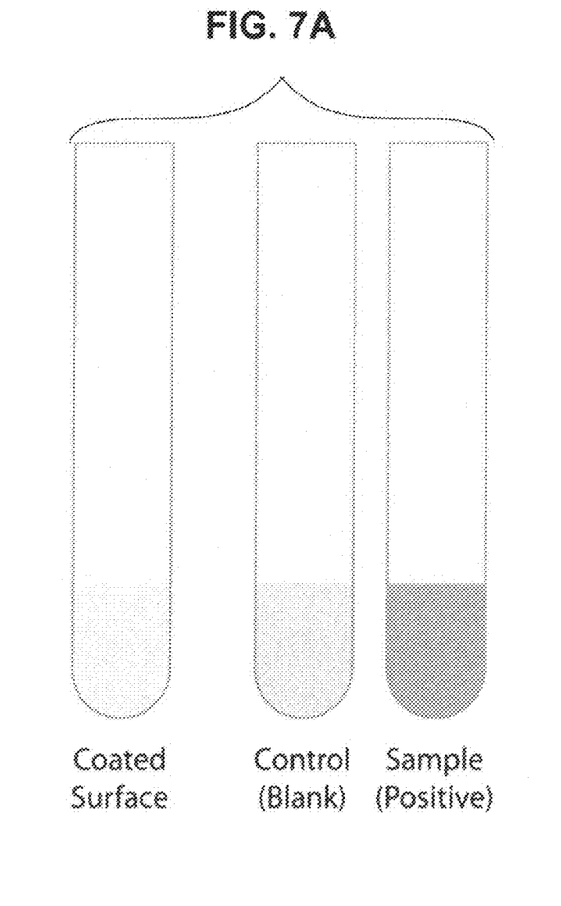
FIG. 7 shows various configurations of an assay of the subject invention.
Figure 7B:
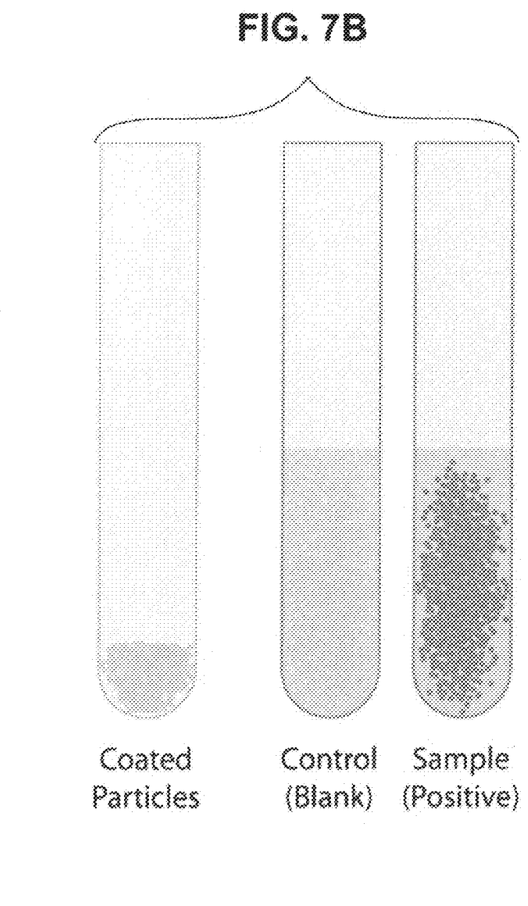

In addition to the coating of flat surfaces, it is possible to coat the inside surfaces of any suitable vessel or the surface of particles such that color development is visualized as a change in vessel color or particle color (FIG. (7)). Thus, one embodiment of the system comprises particles that are of size such that a change in their color is perceived as a change in the color of the entire solution.

FIG. 7 shows vessel configurations of a multilayered thin-film diagnostic device. (A) The inside surface of a vessel may be coated with the thin films, thus producing a darkened wall in the presence of sufficient proteolytic activity. (B) Particles may also be coated in a multilayered manner and, thus, change color in a positive test.

Rapid quantitative/qualitative detection minimize time and increase productivity; assays can be developed for naked eye or quantitative assessment using well established, relatively inexpensive detection technologies; easy-to-interpret detection system when used by non-technical personnel; positive color development correlates to positive test; multiple analytes can be assayed at once; suitable for use in a number of physical interpretation including monolithic films, coated vessel surface, coated particles, multi-colored assays, etc.

EXAMPLE 6

FRET Assay Diagnostic Device

In one embodiment, the subject invention provides methods and devices for rapid and accurate, quantitative and/or qualitative, measurement of protease by utilizing a FRET assay format.

As shown in FIG. 1, this device can comprise various components including, for example, (1) a buffer storage chamber, (2) elution buffer, containing a peptide substrate, (3) a snap valve, (4) an elution and reaction chamber, (5) a cap separating the buffer storage chamber and the reaction chamber, (6) a hollow swab-suspension shaft, (7) a sample collection swab, (8) a stop and read chamber containing anti-substrate peptide antibody, (9) a thin foil divider separating the elution and reaction chamber and the stop and read chamber.

In one embodiment, the hollow swab-suspension shaft comprises a hollow straw and a cotton swab, and the hollow straw the buffer storage chamber and the swab.

This assay can be practiced in the following steps, (1) apply the swap to wound debridement and collect wound fluid sample; (2) pull the snap valve to release elution buffer containing peptide substrate. As elution buffer drains down the straw to perfuse the swab, wound sample is eluded from the swab, making MMPs in wound fluid available to peptide substrate for proteolysis; (3) wait for the proteolysis reaction; (4) push down the swab to perforate the thin foil divider, allowing the reaction mixture into the stop and read chamber (the anti-protease antibody binds to the protease and stop the reaction); (5) insert the entire device into a fluorimeter to read the result.

The peptide substrate can be a flurophore-labeled soluble peptide, containing a fluorescing dye, a quencher in proximity to the fluorescing dye, and a protease cleavage site between the fluorescing dye and the quencher.

In one embodiment, the peptide substrate contains a cleavage site for MMP-9, to indicate when MMP-9 protease activity levels are elevated in samples of wound fluid.

In a specific embodiment, the peptide sequence is GABA-Proline-Glutamine-Glycine-Leucine-Lysine-Alanine-Lysine-NH$_2$ (SEQ ID NO:1).

Examples of variants of the substrate are as follows:

Where the numbers are locations where substitutions can be made.

(1). GABA is a four carbon spacer, other spacers with one more or one less carbon can be used.

(2) Lys. The primary function of this amino acid is to connect to a fluorescent dye and, as such, it can be, for example, Glu, Asp, Lys, Arg, or Cys as long as the fluorophore chosen has the correct coupling chemistry.

In a further specific embodiment the FRET receiver dye is Dabcyl and is attached at the amino-terminus to the Gamma-aminobutyric acid (GABA) moiety. The fluorophore is 5-carboxyfluorescein (5-FAM) and is attached to the epsilon amine group of lysine at position 6 of this octamer (counting GABA).

Other combinations of quencher and fluorophore can be used. One embodiment uses a dual fluorescein pair (both fluorophore and quencher). The advantage of this is having two fluorophores per cleavage. Another specific option is to utilize a fluorescein/rhodamine pair. This results in a change in fluorescence color with cleavage.

Other embodiments include the use of variants of fluorescein (e.g. 5 FAM, 6 FAM, and regular fluorescein) or other xyanthene fluorophores (rhodamines, etc).

For Lys, or any other amino acid analog that possesses at least one free primary amine, the following fluorescein-based molecules can be used to produce comparable results: 5-fluorescein isothiocyanate (5-FITC), 6-fluorescein isothiocyanate (6-FITC), or 5/6-FITC mixed isomers, 5-carboxyfluorescein (5-FAM), 6-carboxyfluorescein (6-FAM), 5/6-FAM mixed isomers, 5-carboxyfluorescein N-hydroxysuccinimidyl ester (5-fluorescein-SE), 6-carboxyfluorescein N-hydroxysuccinimidyl ester (6-fluorescein-SE), or 5/6-fluorescein-SE mixed isomers.

For Glu, Asp, or any other amino acid analog that possesses at least one free carboxylic acid, then any fluorescein derivatized with a primary amine can be used.

For Cys or any other amino acid analog that possess at least one free sulfhydryl group, 5-maleimide fluorescein (5-MF), 6-maleimide fluorescein (6-MF), or 5/6-MF mixed isomers, 5-iodoacetamidofluorescein (5-IAF), 6-iodoacetamidofluorescein (6-IAF), or 5/6-IAF mixed isomers can be used.

Finally, rhodamine 110 with the various coupling chemistries mentioned above can be used because it is 1) green fluorescent (i.e. similar spectral characteristics) and 2) a xanthene dye (i.e. similar shape).

The quencher is constrained by two primary requirements: compatibility with the protease (e.g. shape) and spectral characteristics (e.g. compatibility with the fluorophore) (limited success has been achieved using xanthene dyes as quenchers (5-FAM and rhodamine).

The antibody binds to the protease, or to the peptide substrate, and stops the cleavage reaction. In one embodiment, the antibody is an anti-MMP antibody. Additionally, adding chemicals such as EDTA into the stop and read chamber can assure complete stop.

This device provides a method of rapid quantification of protease activities in wound tissue. In one embodiment which the peptide cleavage site is MMP-9, the incubation time of the proteolysis reaction is around 10 minutes. Therefore, by using this device, the caregiver is able to quantify the level of protease activity in the actual wound in a short time and give necessary treatment immediately.

All patents, patent applications, provisional applications, and publications referred to or cited herein, supra or infra, are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application.

We claim:

1. A method for detecting a target protease in a biological sample wherein said method comprises the following steps:
   a) providing a substrate to which is attached a fluorescing dye and a dye that quenches fluorescence (quencher), wherein the substrate has SEQ ID NO:1, the fluorescing dye and the quencher are in sufficiently close proximity on the substrate such that the quencher quenches the fluorescence of the fluorescing dye, and wherein the two dyes are separated by a site that is cleaved by the target protease such that, when the target protease cleaves the substrate the fluorescing dye is separated from the quencher,
   b) contacting the substrate with the sample for a period of time sufficient to permit substrate cleavage to occur if there is protease present in the sample;
   c) subjecting the sample to non-ionizing electromagnetic radiation that causes the fluorescing dye to fluoresce; and
   d) detecting any fluorescence,
   wherein the detection of fluorescence indicates that protease is present in the sample.

2. The method, according to claim 1, wherein the target protease is one or more matrix metalloproteinases.

3. The method, according to claim 2, wherein the one or more matrix metalloproteinases is MMP-9.

4. The method, according to claim 1, wherein the fluorescing dye is a fluorescein compound.

5. The method, according to claim 1, wherein the quencher is Dabcyl.

6. The method, according to claim 1, wherein there is more than one fluorescing dye and/or more than one quencher.

7. The method, according to claim 1, wherein results are obtained in less than 10 minutes.

8. The method, according to claim 1, wherein said method gives a quantitative indication of the amount of protease present in the sample.

9. The method, according to claim 1, wherein the target protease is endogenous.

10. The method, according to claim 1, wherein said biological sample is taken from a wound.

11. The method, according to claim 10, wherein the wound is a chronic wound.

12. The method, according to claim 1, wherein the contacting step is carried out in the same container as the fluorescence detection step.

13. The method, according to claim 1, wherein protease activity can be detected in the presence of blood.

14. The method, according to claim 1, wherein multiple proteases are detected.

15. The method, according to claim 1, wherein the fluorescing dye is 5-carboxyfluorescein and the quencher is Dabcyl.

16. The method, according to claim 1, wherein the cleavage of the substrate by the target protease is terminated by adding an antibody to the target protease.

17. A method for detecting a target protease in a biological sample wherein said method comprises the following steps:
   a) providing a substrate to which is attached a fluorescing dye and a dye that quenches fluorescence (quencher), wherein the substrate has SEQ ID NO:1, wherein the fluorescing dye and the quencher are in sufficiently close proximity on the substrate such that the quencher quenches the fluorescence of the fluorescing dye, and wherein the two dyes are separated by a site that is cleaved by the target protease such that, when the target protease cleaves the substrate the fluorescing dye is separated from the quencher,
   b) contacting the substrate with the sample for a period of time sufficient to permit substrate cleavage to occur if there is protease present in the sample;
   c) subjecting the sample to non-ionizing electromagnetic radiation that causes the fluorescing dye to fluoresce; and
   d) detecting any fluorescence;
   wherein the detection of fluorescence indicates that protease is present in the sample; and wherein the biological sample is collected in a hollow straw through which a solution containing the substrate travels until it contacts a portion of a swab with the biological sample, after which the swab is inserted into another chamber in which the fluorescence detection step takes place.

18. A method for visualizing the spatial distribution of protease activity in a wound bed, wherein said method comprises the following steps:
   a) providing a thin film substrate comprising at least one protease substrate, wherein the substrate has SEQ ID NO:1;
   b) applying an absorbent pad to a wound to obtain a biological sample from the wound;
   c) contacting the thin film with the absorbent pad for a sufficient period of time to permit digestion of the target substrate(s) by proteases present in the biological sample; and
   d) visualizing, on the thin film substrate the sites of substrate digestion, wherein said visualization is achieved by a chromogenic-, luminescence-, or fluorescence-based detection system.

* * * * *

UNITED STATES PATENT AND TRADEMARK OFFICE
CERTIFICATE OF CORRECTION

PATENT NO. : 8,058,024 B2
APPLICATION NO. : 12/316705
DATED : November 15, 2011
INVENTOR(S) : Gregory S. Schultz et al.

It is certified that error appears in the above-identified patent and that said Letters Patent is hereby corrected as shown below:

Column 5,
Line 14, "calorimetric assays." should read --colorimetric assays.--

Signed and Sealed this
Fifth Day of February, 2013

Teresa Stanek Rea
*Acting Director of the United States Patent and Trademark Office*

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Peptide Substrate
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Pro Gln Gly Leu Lys Ala Lys
1               5